United States Patent
Morris et al.

(10) Patent No.: US 8,076,118 B2
(45) Date of Patent: Dec. 13, 2011

(54) LIVE WATER COMPOSITIONS FOR BIO-CYCLING OF AQUARIUMS

(76) Inventors: Barrington A. Morris, Coral Springs, FL (US); Eric A. Goulbourne, Jr., Hamilton, OH (US)

( * ) Notice: Subject to any disclaimer, the term of this patent is extended or adjusted under 35 U.S.C. 154(b) by 577 days.

(21) Appl. No.: 10/955,257

(22) Filed: Sep. 30, 2004

(65) Prior Publication Data

US 2005/0076850 A1    Apr. 14, 2005

Related U.S. Application Data

(63) Continuation-in-part of application No. 10/883,576, filed on Apr. 28, 2004, now abandoned, which is a continuation of application No. 09/978,947, filed on Oct. 16, 2001, now Pat. No. 6,939,708, which is a continuation of application No. 09/438,672, filed on Nov. 12, 1999, now Pat. No. 6,376,229.

(60) Provisional application No. 60/117,959, filed on Jan. 29, 1999.

(51) Int. Cl.
*C12N 1/20* (2006.01)
*C12N 1/04* (2006.01)
*C12N 1/00* (2006.01)

(52) U.S. Cl. ..................................... 435/252.1; 435/260

(58) Field of Classification Search ................ 435/256.8
See application file for complete search history.

(56) References Cited

U.S. PATENT DOCUMENTS

| | | | |
|---|---|---|---|
| 3,860,490 A | 1/1975 | Guttag | |
| 4,226,210 A * | 10/1980 | Lockwood et al. | 119/236 |
| 4,874,707 A | 10/1989 | Bock | |
| 4,990,449 A | 2/1991 | Caissel | |
| 4,999,301 A | 3/1991 | Bryan-Jones | |
| 5,314,542 A | 5/1994 | Cassidy | |
| 5,733,774 A | 3/1998 | Jin | |

OTHER PUBLICATIONS

Shpigel et al. "Acclimation and propagation of abalone *Haliotis tuberculata* in a land-based culture system in Israel". Journal of the World Aquaculture Society. 1996. vol. 27, No. 4, pp. 435-442.*

* cited by examiner

*Primary Examiner* — Vera Afremova
(74) *Attorney, Agent, or Firm* — Mark D. Bowen, Esq.; Malin Haley DiMaggio Bowen & Lhota, P.A.

(57) ABSTRACT

Live water solutions containing natural fresh water or saltwater microorganisms, is used in the bio-cycling of aquariums and to provide a healthy aquatic environment. Live water obtained from natural bodies of water, such as an ocean, sea, lake, river, or stream is filtered through filter media having a pore size between 5 and 20 microns to remove contaminants and debris while allowing microorganisms to remain in suspension. The live water is packaged in containers for retail sale thereby providing consumers with a source of live aquarium water for use in an aquarium during initial set-up, to replace water lost to evaporation, and for effecting quick water changes. An enrichment solution is disclosed to aid in maintaining the microorganisms metabolically and physiologically viable for extended periods. In an alternate embodiment, the live water is concentrated to a salinity level not less than 0.8 $a_w$ thereby reducing volume while maintaining microorganism viability. Rapid biochemical cycling of an aquarium is achieved by introducing the live water into an aquarium whereby marine microorganisms instantly contribute to establishing a healthy aquatic environment by reducing harmful ammonia levels and through denitrification.

4 Claims, 5 Drawing Sheets

Figure 1

Sea Water Enrichment Solution

To 940 mL of sea water add:

| Quantity | Compound | Stock Solution |
|---|---|---|
| 1.0 mL | $NaNO_3$ | 75.0 g/L of distilled water |
| 1.0 mL | $NaH_2PO_4 \cdot H_2O$ | 5.0 g/L of distilled water |
| 1.0 mL | Trace Metal Solution | (see Figure 2) |
| 0.5 mL | Vitamin Solution | (see Figure 3) |
| 50 mL | Organics Stock Solution | (see Figure 4) |

Make final volume up to 1.0 L with sea water. Filter sterilize after all additions.

Figure 2

Trace Metal Solution

To 950 mL of distilled water add:

| Quantity | Compound | Stock Solution |
|---|---|---|
| 3.15 g | $FeCl_3 \cdot 6H_2O$ | - |
| 4.36 g | $Na_2EDTA \cdot 2H_2O$ | - |
| 1.0 mL | $SrCl_2 \cdot 6H_2O$ | 9.8 g/L distilled water |
| 1.0 mL | $K_2MoO_4 \cdot 2H_2O$ | 6.3 g/L distilled water |
| 1.0 mL | $ZnSO_4 \cdot 7H_2O$ | 22.0 g/L distilled water |
| 1.0 mL | $CoCl_2 \cdot 6H_2O$ | 10.0 g/L distilled water |
| 1.0 mL | $MnCl_2 \cdot 4H_2O$ | 180.0 g/L distilled water |

Make final volume up to 1.0 L with distilled water. Filter sterilize.

Figure 3

Vitamin Solution

To 950 mL distilled water add:

| Quantity | Compound | Stock Solution |
|---|---|---|
| 1.0 mL | Vitamin B12 (Cyanocobalamin) | 1.0 g/L of distilled water |
| 10.0 mL | Biotin | 0.1 g/L of distilled water |
| 200.0 mg | Thiamine HCl | - |

Make final volume up to 1.0 L with distilled water. Filter sterilize into plastic vials and store in refrigerator.

Figure 4

Organics Stock Solution

To 900 mL of distilled water add:

| Quantity | Compound |
|---|---|
| 1.0 g | Sodium Acetate |
| 6.0 g | Glucose |
| 3.0 g | Sodium Succinate |
| 4.0 g | Peptone |
| 2.0 g | Yeast extract |

Bring up to 1.0 L with distilled water. Filter sterilize and dispense into 50 mL aliquots.

Viable Bacteria Per Pound of Aragonite

| Approximate Date Tested | Log CFU/Pound of Aragonite (with Enrichment Solution) |
|---|---|
| Initial | 7.62 |
| 3 months | 7.57 |
| 6 months | 7.70 |
| 9 months | 7.38 |
| 12 months | 7.32 |

LIVE WATER COMPOSITIONS FOR BIO-CYCLING OF AQUARIUMS

CROSS-REFERENCE TO RELATED APPLICATIONS

This application is a continuation-in-part of U.S. patent application Ser. No. 10/833,576, filed Apr. 28, 2004, which is a continuation of U.S. patent application Ser. No. 09/978,947, filed Oct. 16, 2001, which is a continuation of U.S. patent application Ser. No. 09/438,672, filed Nov. 12, 1999, now U.S. Pat. No. 6,376,229, which claims the benefit of U.S. Provisional Patent Application Ser. No. 60/117,959, filed Jan. 29, 1999, each of which are incorporated herein by reference.

STATEMENT REGARDING FEDERALLY SPONSORED RESEARCH OR DEVELOPMENT

Not Applicable

BACKGROUND OF THE INVENTION

1. Field of the Invention

The present invention relates to the biochemical cycling of freshwater and saltwater marine aquariums, and, more particularly to a method of rapid biochemical cycling of aquariums using live ocean water, live fresh water, or concentrates thereof to enhance the nitrogen cycle in order to rapidly denitrify the aquatic environment and to establish biochemical conditions that are favorable to the survival and viability of fish, crustaceans, invertebrates, and other aquatic life.

2. Description of Related Art

Aquariums have experienced a boom in popularity in recent years. Many saltwater and freshwater aquariums include a diverse mix of tropical fish, live coral formations, and other exotic marine life. Aquatic life is directly affected by the chemical, biological, and physical characteristics of their environment. A number of environmental factors are critical to maintaining the delicate balance required for a healthy aquarium environment. Water temperature, pH level, lighting conditions, and complex chemical balances must constantly be maintained and monitored. The introduction of waste from fish and other marine life in an aquarium causes a series of chemical changes often resulting in chemical imbalances that are not conducive to aquatic life. It is therefore crucial to maintain a high level of water quality to provide a healthy aquatic environment.

The initial set up of a marine aquarium typically requires a "conditioning period" that can take up to six (6) weeks depending upon the aquarium conditions and temperature. During the conditioning period the chemical composition of the water undergoes a series of changes and waste products can quickly build-up to levels that are toxic to aquarium life. The introduction of fish, plants, and food into an aquarium begins a natural process often referred to a "biochemical cycling".

A significant change in the chemical composition of the water involves the accumulation of ammonia. The process begins when fish and invertebrates excrete waste. The excreted waste, and decaying food and organic compounds, increases the amount of ammonia present in the water. Harmful ammonia and nitrite are constantly converted into less harmful nitrates, which in turn is used by plants and algae for food. Aquariums are full of both autotrophic and heterotrophic bacteria that attach, grow, and form biofilm colonies wherein the bacteria convert toxic nitrogeneous compounds and ammonia into harmless products. *Nitrobacter* and *Nitrosomonas* are examples of autotrophic bacteria that use oxygen to oxidize ammonia ($NH_4$) to nitrite ($NO_2$) and Nitrate ($NO_3$).

Ammonia is a toxic waste product which, if unchecked, can accumulate and cause injury or death to aquarium inhabitants. In fact, the presence of ammonia in aquarium water is the main cause of death in aquarium fish. The primary sources of ammonia are decaying organic material (such as uneaten food) and waste excreted by fish, other animals and organisms. An ammonia level as low as 0.5 parts-per-million (PPM) creates stress in fish and compromises the natural immune systems of fish and other aquarium inhabitants. An ammonia level of 2 PPM has been found to cause the natural immune system of the fish and other aquarium inhabitants to fail or otherwise cease functioning. Accordingly, maintaining ammonia levels is critical to the health of the aquarium habitat.

The accumulation of ammonia is often caused by the lack of sufficient numbers of *Nitrosomonas*. *Nitrosomonas* is a genus of bacteria in aquaria that oxidize ammonia thereby regulating the ammonia level. *Nitrosomonas*, and other ammonia oxidizing bacteria, are found in natural abundance in natural ocean water and fresh water, in marine materials, such as sand, aragonite, and crushed coral, harvested from the ocean floor. Nature provides many types of bacteria that, in the presence of oxygen, carry out the oxidation of ammonia to nitrites and eventually to nitrates in a process known as nitrification. It has been found that such bacteria settle on marine materials, such as aragonite (reef sand), and eventually form a biofilm. Marine nitrifying bacteria in the biofilm oxidize ammonia to nitrite, and nitrite to nitrate. Accordingly, these natural marine materials provide a natural source of ammonia oxidizing bacteria for use in maintaining ammonia levels in aquarium environments. Nitrate not utilized by plants is removed by other bacteria in the absence of oxygen (the anaerobic environment found in the lower levels of the sediment) in a process called denitrification.

While marine nitrifying bacteria are found in abundance in natural materials, such as aragonite harvested from the ocean floor, it has been found that there are generally three conditions that are required to maintain the nitrification process. These conditions are: (1) a surface upon which bacteria can attach, grow, and form a biofilm; (2) ammonia to start the process; and (3) an aerobic environment. The absence of any of the above-referenced conditions will either prevent or delay the nitrification process.

The initial set-up of aquariums presents unique biochemical circumstances that must be addressed in order to produce and maintain a healthy environment for marine life. The initial cycling of organic compounds in an aquarium started with dry sand or gravel often takes a period of several weeks during which an ammonia source (often only one or two small fish). provides an environment wherein beneficial bacteria to establish and begin to flourish eventually forming a biofilm. It has been found that the long initial cycling period realized when starting an aquarium with dry sand or gravel results from the time required for bacteria to attach, grow and form a biofilm on the previously dry, and organically inactive, sand and gravel. It has been shown that the initial cycling period can be substantially reduced by the introduction of natural marine bacteria. There are various sources of marine bacteria, including bacteria present in natural seawater, and bacteria-rich "wet" sand and gravel that has been recently harvested from the ocean and thus contains an abundance of bacterial biofilm. Marine sand and gravel harvested from the ocean or riverbeds contain both autotrophic and heterotrophic bacteria in their natural state (i.e. established biofilms on the sand particles), each of which facilitate the rapid cycling of an aquarium.

Accordingly, there exists a need for a method of harvesting and packaging marine materials, such as live ocean water, live fresh water, and substrate material such as aragonite reef sand, gravel, crushed coral and the like, such that the bacteria remain metabolically and physiologically active for extended periods of time in excess of twelve (12) months in retail packaging at room temperature. There further exists a need for a method of introducing a harvested and packaged natural granular marine substrate material into an aquarium such that the biochemical cycling process performs rapidly, and the aquatic life is stabilized and maintained naturally.

It has proven difficult, however, to maintain ammonia oxidizing bacteria and other useful bacteria in a biologically active state during the extended period beginning with the harvesting of the material and ending with the purchase by a consumer and delivery into an aquarium; a time period often reaching up to six (6) months or more. The difficulty is increased where the harvested materials must be stored for extended periods in retail packaging at room temperatures. It has also proven difficult to provide a rapid biochemical cycling method containing an abundance of marine bacterial biofilm that closely resembles the natural ocean process in a miniature ecosystem such as an aquarium.

The background art reveals several references directed to preserving bacteria and the like, but none of the references adequately address the problems encountered in maintaining ammonia oxidizing bacteria in a bio-actively viable bio-film for extended periods. The background art also reveals several references directed to the biochemical cycling process involving artificial and external filtration methods, however, none adequately address the problems encountered when attempting to easily and effectively introduce natural granular substrate material into an aquarium, whereby rapid bio-cycling occurs, promoting a healthy and stable environment for aquatic life.

U.S. Pat. No. 4,874,707, issued to Bock, discloses a complex laboratory process for producing an aqueous suspension of nitrifying bacteria using a growth medium containing ammonia or nitrite, in which the bacteria remain metabolically and physiologically active even after a storage period of one year or more at 30° C. (i.e. approximately room temperature). According to Bock, air, pure oxygen, or a mixture of air and pure oxygen is passed through a gas permeable non-porous tube submerged in a suitable culture medium. As a result of positive aerotaxis, nitrifying bacteria adhere on the tube surface, forming a biofilm of extracellular polymers. The bacteria are grown in the dark at a constant temperature of 30° C. When a stationary growth phase has been reached the oxygen supply is stopped.

U.S. Pat. No. 4,999,301, issued to Bryan-Jones, a method whereby microorganisms are stored for long periods of time in storage mediums containing a high concentration of nutrients and growth inhibiting substances to maintain the microorganisms, such as bacteria, in the stationary phase of their growth cycle. The concentrated medium disclosed by Bryan-Jones contains an excess of essential nutrients while the microorganisms are in the "death phase." When the concentrated medium is diluted to below the concentration that inhibits microorganism growth, the microorganisms will start to increase in number and grow. The claims of the Bryan-Jones reference are limited to bacteria selected from the group comprising *Lactobacillus plantarum* and *Bacillus subtilus*. E.g. claim 1. In addition, the '301 patent claims a bacterial culture kit having bacteria in a growth medium comprising from 10% to about 30% solids which function to delay the onset of the normal "death phase". The solids are disclosed as waste products from a food manufacturing process or an alcohol fermentation process. See, e.g. Column 2, lines 46-58. Bryan-Jones discloses a storage medium consisting of wheat spent wash syrup and acetate/acetic acid buffer and sucrose. Bryan-Jones claims that an advantage of such a kit is that a sufficient number of the microorganisms will remain viable when the kit is sold to a consumer such that the microorganisms will start to increase in number and grow after purchase.

U.S. Pat. No. 5,314,542, issued to Cassidy et al., discloses a culture of *Nitrosomonas* packaged in a manner to induce a metabolic state of dormancy under conditions favorable for survival of up to at least one year at room temperature. Upon obtaining culturing media with the maximum obtainable cell concentration, the media is concentrated to approximately one twenty-fifth ($1/25$) of its volume by centrifugation or filtration. See Col. 3, lines 5-9. The concentrate is re-suspended in sterile water of "suitable salinity" and packaged in sterile opaque containers wherein Cassidy et al. claim that the cells will remain viable for at least one year. According to Cassidy et al., the majority of the re-suspended cells packaged in this manner enter a metabolic state of inactivity (i.e. dormancy). The disclosure further states that the preserved cells can at any time be returned to their metabolically active state by adding ammonium chloride (or other suitable salt) to the opaque container to bring the ammonia concentration to about 200 ppm. There is also disclosed a method for rapid reactivation to complete metabolic activity within about 72 hours and subsequent addition into aquaria to begin oxidation and prevention of harmful ammonia accumulation in aquaria.

U.S. Pat. No. 5,733,774, issued to Jin et al., discloses stabilized bacteria that can survive long term storage at high temperatures. According to the method disclosed by Jin et al., bacteria are dried until they reach a dormant state. Suitable methods include air-drying, vacuum drying etc. See, Col. 2, lines 1-3. Next Oxygen is then removed from the environment surrounding the bacteria to prevent oxidative damage to the dormant cells. The bacteria is then packaged and stored in material impermeable to gas and water vapor, whereby Jin claims the bacteria will remain stable and efficacious for at least a year.

Several patents have been issued in reference to biochemical cycling and filtration methods. U.S. Pat. No. 3,957,634, issued to Orensten, et al., discloses a filtration means and method for aquarium systems in which water in the tank is purified in a biological/mechanical external filtration device. The biological portion of the filtering process contains nitrifying bacteria to assist in keeping the ammonia concentration in the aquarium system at a safe, nontoxic level.

U.S. Pat. No. 5,269,914, issued to Englert, discloses an undergravel filtration system for an aquarium that assists in the removal of toxic waste products in the tank by creating and maintaining colonies of aquatic anaerobic bacteria.

U.S. Pat. No. 5,679,253, issued to Fuerst, et al., discloses a rotating biological aquarium filter system that fosters the growth of aerobic bacteria on the surface of the filter body, reducing the level of toxins within the aquarium water.

U.S. Pat. No. 5,746,921, issued to Gargas, et al., discloses a fluidized bed aquarium filtration method for removing chemical and physical waste from an aquarium. The fluidized bed can include particles, such as sand, for removing ammonia from the water.

In my U.S. Pat. No. 6,376,229, methods and compositions are disclosed for use in rapid bio-cycling of aquaria. We disclose the harvesting, and packaging of natural marine bacterial biofilm associated with marine sediments (e.g. live sand, live aragonite, etc.), packaging methods and compositions for preserving metabolic and physiological activity, and use of marine sediments to rapid cycle marine aquariums.

The background art, however, fails to teach or suggest the use of "live" ocean water or live fresh water to jump start or enhance the nitrogen cycle and rapid bio-cycling of aquaria. More particularly, ocean water and fresh water each contain microscopic organisms, such as *Nitrobacter* and *Nitrosomonas* autotrophic bacteria that use oxygen to oxidize ammonia ($NH_4$) to nitrite ($NO_2$) and Nitrate ($NO_3$).

Accordingly, there exists a need for a method of rapid cycling an aquarium using preserved ammonia-oxidizing bacteria available to consumers via retail sale and use in connection with saltwater and fresh water aquaria. Furthermore, the background art fails to disclose a biochemical cycling method that includes the use of naturally occurring bacteria present in water (i.e. live water) obtained directly from a body of water, such as the ocean, lake, river, or stream.

BRIEF SUMMARY OF THE INVENTION

It is an object of the present invention to provide a method for preserving saltwater and freshwater marine organisms for extended periods of time such that the organisms remain capable of metabolic and physiologic activity upon introduction into a marine aquarium during initial set-up. It is also an object of the present invention to provide various compositions for use in rapid bio-cycling of marine aquariums.

A. Live Sand Embodiment

One aspect of the invention relates to a method for rapid cycling of a marine aquarium using packaged marine substrate material, such as sand, aragonite, coral rock and crushed coral in an aqueous solution, suitable for retail display and sale, wherein a suitable environment is present so that marine microorganisms remain in biofilms attached to the surface of the material for extended periods of time. A further aspect of the invention relates to the discovery of a nutrient rich seawater enrichment solution containing vitamins, organics stock, trace metals, and $NaNO_3$ and $NaH_2PO_4H_2O$ for further extending the period of time wherein the organisms remain bioactive. Yet another aspect of the invention relates to a method for the introduction of naturally preserved granular marine substrate material containing live marine bacteria into an aquarium, wherein a suitable environment is present thereby enabling rapid biochemical cycling of organisms. Still another aspect of the invention relates to the survival of sensitive fish and invertebrates in captivity due to a naturally duplicated ecosystem and biochemical cycling process that maintains proper water chemistry necessary for aquatic life.

The invention provides for the effective harvesting, packaging, transport, bio-active storage, and retail sale of aquarium substrate material containing live microorganisms, such as bacteria useful in oxidizing ammonia in aquariums, whereby the microorganisms remain biologically viable for extended periods of time in excess of twelve (12) months thereby maintaining a stable and healthy aquarium environment. The invention further provides for the effective and easy introduction of natural granular substrate material into an aquarium, thereby reducing harmful nitrates, maintaining proper pH, providing enhanced buffering capacity and essential inorganic elements which encourage a stable and healthy environment for aquatic life for extended periods of time.

Another object of the present invention is to provide a method for harvesting and packaging marine substrate material with an optimal amount of seawater and air in packaging specifically configured for maintaining ammonia-oxidizing bacteria in a state wherein the bacteria are capable of metabolic and physiologic activity after a prolonged period, at room temperature.

Still another object of the present invention is to provide an enrichment solution for prolonging the bio-active shelf life of marine microorganisms present in packaged marine substrate materials, such as aragonite, crushed coral, and sand.

Yet another object of the present invention is to provide a method for harvesting and packaging bio-actively optimal quantities of marine substrate material, air, seawater, and an enrichment solution for maintaining marine organisms in a biologically viable state for extended periods of time.

Still another object of the present invention is to provide packaging material that is specifically sized for prolonging the bio-active state of marine organisms when packaged in certain optimal quantities.

Yet another object of the present invention is to provide a method and composition for the preservation of microorganisms, associated with sand, shells, and coral materials harvested from natural marine environments, whereby the materials may be packaged in sealed containers, suitable for retail sale, within a unique enriched seawater solution.

Still another object of the present invention is to provide a method for introducing naturally preserved granular marine substrate material containing active biofilm into a water-filled aquarium, whereby the biochemical cycling process is permitted to occur rapidly and effectively, further allowing nitrogenous waste to be properly removed while maintaining proper pH.

Yet another object of the present invention is to provide for the extended survival of sensitive fish and invertebrates in aquariums for indefinitely long periods of time due to a naturally duplicated ecosystem promoting the rapid biochemical cycling process that maintains the proper water chemistry necessary for aquatic life.

B. Live Water Embodiment

A further aspect of the present invention relates to providing live water for use in aquariums. In this regard, the present invention provides a natural live seawater (or alternatively freshwater) composition that includes all of the common chemical and biological properties and characteristics of water found in a healthy aquatic environment. In alternate embodiment, the live water is supplemented with an enrichment solution to aid in preserving metabolic and physiologic activity of the microorganisms contained within the water. In yet another embodiment the live water is processed for purity. In still another embodiment the live water is in a concentrated state.

It is very important in the maintenance of a marine aquarium that the environment be replenished regularly. The best means of accomplishing this is to change at least 15 percent of the water once a month. The ideal replacement water is 100% natural ocean water, or alternatively fresh water in the case of a fresh water aquarium. Natural ocean water containes all the essential elements and micronutrients required by fish, coral and invertebrates that inhabit an aquarium. In addition, natural ocean water contains live bacteria necessary for the rapid removal of biologic waste. It is estimated that there are over 11,000,000 live bacteria per gallon of ocean water.

Accordingly, it is an object of the present invention to provide live water for use in enhancing an aquatic environment.

Another aspect of the present invention is to provide a live water concentrate for use in enhancing an aquatic environment.

Still another object of the present invention is to provide a method of processing and packaging ocean water and freshwater for sale in retail packaging.

In accordance with these and other objects that will become apparent hereinafter, the instant invention will now be described with particular reference to the accompanying drawings.

BRIEF DESCRIPTION OF THE SEVERAL VIEWS OF THE DRAWINGS

FIG. 1 shows a formula for a seawater enrichment solution according to the present invention;

FIG. 2 shows the formula for the trace metal solution referenced in FIG. 1;

FIG. 3 shows the formula for the vitamin solution referenced in FIG. 1;

FIG. 4 shows the formula for the organics stock solution referenced in FIG. 1;

DETAILED DESCRIPTION OF THE INVENTION

Figure 5:
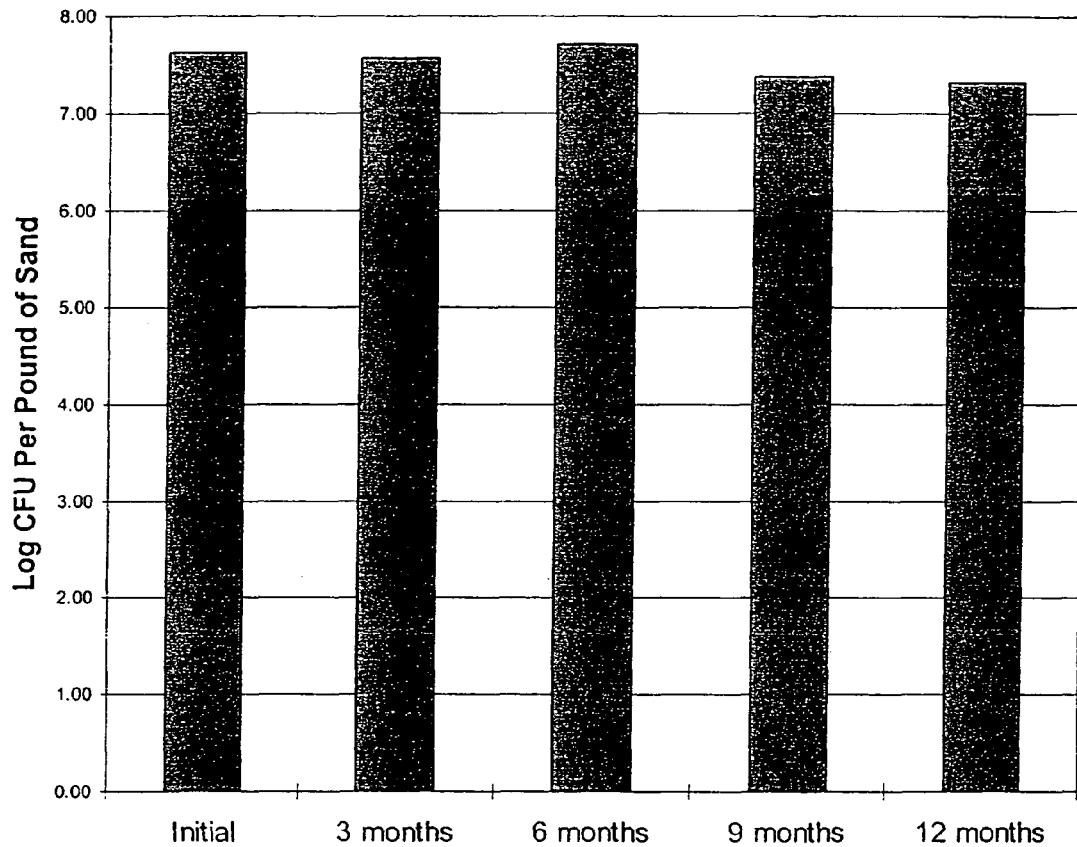
FIG. 5 is a graph depicting the number of colony forming units per pound ("CFU/Pound") of aragonite sand measured along the Y-axis and time in months measured along the X-axis as found on average in two different bags of aragonite packaged with an enrichment solution according to the present invention.

According to a first aspect of the present invention there is disclosed a method for rapid cycling an aquarium using preserved saltwater marine microorganisms, harvested from a natural marine environment, by introduction into an aquarium environment to facilitate rapid biochemical cycling. As used herein the term "marine microorganisms" and/or "microorganisms" shall mean aquatic bacteria naturally found in saltwater environments.

I. Live Sand Embodiment

Specifically, the method provides for the harvesting materials that are naturally rich with bacteria, such as sand, shells, aragonite, crushed coral materials, river rocks and pebbles and the like, harvested from submerged marine and/or river environments, and packaging the harvested materials in specifically sized sealed containers, suitable for storage at room temperature and retail sale, such that marine bacteria are preserved in their natural habitat—in biofilms attached to the granular surfaces—for extended periods of time. The method provides the aquarium industry with a useful means for prolonged storage of marine materials while maintaining microorganism bio-activity (i.e. metabolic and physiologic activity) such that, upon introduction into an aquarium environment the microorganisms are effective in biochemical cycling of the aquarium environment and stabilizing ammonia levels thereby resulting in an aquarium environment which is optimal for fish and other living organisms. According to a second aspect of the present invention there is disclosed an enrichment solution for further extending the period of time that the microorganisms remain bio-actively viable. The enrichment solution may be used in combination with the method of the first aspect of the invention to further enhance the period of time that microorganisms remain bio-actively viable. According to a third aspect of the present invention there is disclosed a method for introducing naturally preserved saltwater marine microorganisms into an aquarium environment to facilitate rapid biochemical cycling. According to a fourth aspect of the present invention there is disclosed a method providing for the extended survival of sensitive fish and invertebrates in aquariums due to a naturally duplicated ecosystem promoting the rapid biochemical cycling process thereby maintaining proper water chemistry necessary for aquatic life.

A first aspect of the present invention includes packaging marine substrate materials, such as aragonite, sand, crushed coral and the like according to the following steps:

1. Harvesting marine substrate material from a submerged marine environment;
2. Packaging the harvested marine material in said packaging along with saltwater and air in the following relative ratios: 1 lb. of sand with 2-12 fluid oz. (preferably between 4-6 fluid oz.) water and 5-100 cm$^3$ (preferably between 10-50 cm$^3$) of air.
3. Sealing the packages in an airtight manner.

It has been found that bacteria associated with marine material harvested and packaged in accordance with the above-referenced method steps is metabolically and physiologically active upon introduction into an aquarium environment. The process thus provides an optimal saltwater preservation solution and packaging method that results in the preservation of autotrophic marine bacteria in their natural habitat, i.e. a biofilm existing on the surfaces of the granular material. It is significant to the rapid cycling of aquarium tanks that the bacteria exist in biofilms as the bacteria in such a state are instantly capable of cycling harmful metabolic endproducts upon introduction into the aquarium environment. In contrast, the introduction of bacteria that has been cultured according to teachings of the background art, or bacteria that otherwise exists in a non-biofilm state, requires a substantial number of days and/or weeks to attach to aquarium materials and form biofilms prior to contributing to aquarium cycling.

Each pound of granular material harvested and packaged according to the present invention contains in excess of 10 million live bacteria. Each of the above-referenced steps contributes to a method of packaging harvested marine material whereby both autotrophic and heterotrophic bacteria survive in sealed packaging for longer periods of time than if packaged without one or more of the steps. According to the third aspect of the present invention, marine materials packaged according to the methods of the present invention are capable, upon introduction into an aquarium environment, of carrying out rapid biochemical cycling essential to the maintenance of a successful aquarium.

The first step provides for harvesting marine substrate material from a submerged marine environment and initially storing the harvested marine material in a sealed container with seawater. Harvesting the marine material, such as sand, from a submerged marine environment, as opposed harvesting dry material such as sand and crushed coral, is critical in obtaining material having an abundance of autotrophic and heterotrophic bacteria flourishing in established biofilm colonies. The material is typically initially stored within a container that may, or may not, be airtight, however, this step is one of practicality and is not deemed an important aspect of the present invention. The harvested sand includes some water such that it has the consistency of mud. Accordingly, any reference to the weight of the sand herein relates to the "wet" weight, e.g. the weight of mud as opposed to dry sand.

The second step requires providing packaging material having specific dimensional parameters such that marine material packaged therein preferably forms a uniform layer between ½-inch and 3-inches in depth. The 3-inch depth maximum limitation is considered important in that it allows both water and gas (contained in the packaging along with the harvested material as discussed below) to diffuse sufficiently through the material thereby providing vital, life-sustaining nutrients to the bacteria at all depths. It should be noted, however, that packaging the harvested material in layers exceeding the preferred 3-inch maximum is not a departure from the present invention as bacteria existing in the region of the top 3-inches of deeper layers will remain capable of metabolic and physiologic activity as described herein.

The third step includes depositing the harvested marine material in the packaging material along with seawater and air in the following relative ratios: 1 lb. of harvested material (e.g. sand, aragonite etc.); 2-12 fluid oz. (preferably between 4-6 fluid oz.) of seawater; and 5-100 cm$^3$ (preferably between 10-50 cm$^3$) of air. The fifth step includes sealing the packaging in an airtight manner.

It has been found that the above-referenced ratios of: (1) harvested material (forming a layer of 3-inches or less); (2) sea water; and (3) air; packaged in a sealed container provides a unique life sustaining environment wherein natural marine bacteria are capable of surviving for extended periods in excess of twelve (12) months. The retail packaging material preferably comprises a suitable plastic (either hard or soft/flexible). The contents of the package may be stored at room temperature without adversely affecting the biological viability of the marine bacteria. After an extended shelf life of twelve (12) months at room temperature, and after setting up the aquarium's filtering system and allowing it to circulate, in accordance with the third aspect of the present invention, the contents of the package may be introduced into the aquarium. This will allow rapid biochemical cycling to begin to remove nitrogenous waste and maintaining and/or restoring a natural organic balance thereby resulting in a healthy aquarium habitat. Further, in accordance with the fourth aspect of the present invention, the survival of sensitive fish and invertebrates in aquariums is extended due to a naturally duplicated ecosystem involving the rapid biochemical cycling process thereby maintaining proper water chemistry necessary for aquatic life.

According to a second aspect of the present invention there is disclosed an enrichment solution for further increasing the number of microorganisms that remain bio-actively viable. The enrichment solution may be used in combination with the method of the first aspect of the invention to further enhance the number of microorganisms that remain bio-actively viable during periods of extended storage. Specifically, a second aspect of the invention includes enriching the seawater used to package harvested marine material, such as sand, aragonite and crushed coral. According to the present invention an enrichment solution may include one or more of the following substances: a buffer; vitamins; proteins and/or amino acids; sugars; trace elements (e.g. minerals); Sodium Nitrate (NaNO$_3$); Sodium Phosphate (NaH$_2$PO$_4$H$_2$O).

In a preferred embodiment according to the second aspect of the present invention a sea water enrichment solution is prepared in accordance with the formula described in FIG. 1, whereby the solutions of FIGS. 2, 3, and 4 are combined with a predetermined quantity of sea water (filtered and sterilized after all additions), with predetermined quantities of Sodium Nitrate and Sodium Phosphate.

It has been found that the critical level of moisture necessary to keep the bacteria viable but dormant for more than six months is from 2 to 12 oz. of fortified, sterile-filtered, sea water per pound of live marine sand. Preferably 4 to 8 oz. of fortified sterile seawater is used. Most preferably, the critical level of moisture is generated by the addition of 6 oz. of fortified sterile-filtered seawater per pound of live marine material (e.g. sand, aragonite etc.). The seawater may be fortified with sterile seawater enrichment solution (FIG. 1; one liter of seawater enrichment solution is added to 100 gallons of seawater) and maintained in a sterile state until used.

It has been found that marine aragonite sand subjected to the process disclosed herein is likely to contain not less than 10,000,000 live heterotrophic bacteria per pound. The process results in a natural product that prevents bio-fouling, and contains live marine autotrophic bacteria to provide a proper inorganic balance. The beneficial characteristics of the process using aragonite sand include: (1) reducing harmful nitrate; (2) maintaining proper pH; (3) providing enhanced buffering capacity; and (4) providing essential inorganic elements such as strontium, cobalt, zinc, and molybdenum. In addition, the following trace elements are provided: Zinc Sulfate; Calcium Chloride, Manganese Chloride; Cobalt Chloride; Copper Sulfate; Sodium Molybdate; Strontium Chloride; Nickel Chloride; Potassium Bromide; and Sodium Silicate.

Attached hereto as Appendix A and B are Applicants' findings, over time, with respect to the amount of live bacteria per gram of marine aragonite reef sand packaged in accordance with the present invention both with the seawater enrichment solution (Appendix A) and without (Appendix B).

II. Live Water Embodiment

According to an alternate embodiment, the present invention provides a live ocean water (or fresh water) product that is naturally rich with bacteria for use with marine aquariums. The live water product is useful in shortening the time required to establish a healthy aquatic environment by providing a natural source of marine bacteria. The live water product is further useful as a source of water for aquarium water changes or filling. In various embodiments, the present invention contemplates obtaining live water from a natural body of water, filtering the water to remove contaminants, enriching the water with a nutrient enrichment solution, and concentrating the water to an acceptable salinity level.

The method provides the aquarium industry with a useful means for prolonged storage of marine microorganisms while maintaining microorganism bio-activity (i.e. metabolic and physiologic activity) such that, upon introduction into an aquarium environment the microorganisms are effective in biochemical cycling of the aquarium environment and stabilizing ammonia levels thereby resulting in an aquarium environment which is optimal for fish and other living organisms. According to a second aspect of the present invention there is disclosed an enrichment solution for further extending the period of time that the microorganisms remain bio-actively viable in a live water solution. The enrichment solution may be used in combination with the method of the first aspect of the invention to further enhance the period of time that microorganisms remain bio-actively viable. According to a third aspect of the present invention there is disclosed a method for introducing naturally preserved saltwater marine microorganisms into an aquarium environment to facilitate rapid biochemical cycling. According to a fourth aspect of the present invention a method is disclosed for processing and packaging live water for use in the aquarium field.

A. Composition of Seawater

1. Elements

Seawater is a solution of salts of nearly constant composition, dissolved in variable amounts of water. There are more than 70 elements dissolved in seawater but only SIX make up greater than 99% of all the dissolved salts; and all occur as ions—electrically charged atoms or groups of atoms:

| | | | |
|---|---|---|---|
| Chloride (Cl): | 55.04 wt % | Sodium (Na): | 30.61 wt % |
| Sulphate (SO$_4$): | 7.68 wt % | Magnesium (Mg): | 3.69 wt % |
| Calcium (Ca): | 1.16 wt. % | Potassium (K): | 1.10 wt. % |

Oceanographers use salinity—the amount (in grams) of total dissolved salts present in 1 kilogram of water—to express the salt content of seawater. Normal seawater has a salinity of 35 grams/kilogram (or liter) of water—also expressed as 35‰. Seawater from Wormly in southern England is used as the international standard for seawater composition.

As well as major elements, there are many trace elements in seawater—e.g., manganese (Mn), lead (Pb), gold (Au), iron (Fe), iodine (I). Most occur in parts per million (ppm) or parts per billion (ppb) concentrations. They are important to some biochemical reactions—both from positive and negative (toxicity) viewpoints.

2. Dissolved Gases in Seawater

Seawater also contains small amounts of dissolved gases (nitrogen, oxygen, carbon dioxide, hydrogen, and trace gases). Water at a given temperature and salinity is saturated with gas when the amount of gas entering the water equals the amount leaving during the same time. Surface seawater is normally saturated with atmospheric gases such as oxygen and nitrogen. The amount of gas that can dissolve in seawater is determined by the water's temperature and salinity. Increasing the temperature or salinity reduces the amount of gas that can be dissolved. Once water sinks below the ocean surface, dissolved gases can no longer exchange with the atmosphere. The amount of gas in a given volume of water may remain unchanged, except by movement of gas molecules through the water—diffusion (slow process), or by the water mixing with other water masses containing different amounts of dissolved gas.

In general, nitrogen and rare inert gases (argon, helium, etc.) behave this way—their concentrations are conservative and only affected by physical processes. In contrast, some dissolved gases are non-conservative and actively participate in chemical and biological processes that change their concentrations. Examples are oxygen and carbon dioxide—released and used at various rates in the oceans, especially by organisms.

3. Processes Contributing to Seawater Composition

Salts dissolved in seawater come from three main sources:
 volcanic eruptions
 chemical reactions between seawater and hot, newly formed volcanic rocks of spreading zones (mid-oceanic ridges)
 chemical weathering of rocks on the continents Volcanic eruptions produce large volumes of gases that eventually reach the oceans—most important are sulphate and chloride. Submarine eruptions at spreading ridges inject gases directly into the oceans; gases from subaerial volcanoes are dissolved in rainfall.

Chemical reactions between hot seawater and recently formed basaltic ocean crust lead to removal of magnesium and some sulphate from the seawater, while other elements like lithium and rubidium are added.

The salinity of seawater is usually 35 parts per thousand (also written as o/oo) in most marine areas. This salinity measurement is a total of all the salts that are dissolved in the water. Although 35 parts per thousand is not very concentrated (the same as 3.5 parts per hundred, o/o, or percent) the water in the oceans tastes very salty. The interesting thing about this dissolved salt is that it is always made up of the same types of salts and they are always in the same proportion to each other (even if the salinity is different than average). The majority of the salt is the same as table salt (sodium chloride) but there are other salts as well. The table below shows these proportions:

| Chemical Ion Contributing to Seawater Salinity | Concentration in o/oo (parts per thousand in average seawater) | Proportion of Total Salinity (no matter what salinity) |
|---|---|---|
| Chloride | 19.345 | 55.03 |
| Sodium | 10.752 | 30.59 |
| Sulfate | 2.701 | 7.68 |
| Magnesium | 1.295 | 3.68 |
| Calcium | 0.416 | 1.18 |
| Potassium | 0.390 | 1.11 |
| Bicarbonate | 0.145 | 0.41 |
| Bromide | 0.066 | 0.19 |
| Borate | 0.027 | 0.08 |
| Strontium | 0.013 | 0.04 |
| Fluoride | 0.001 | 0.003 |

Other less than 0.001 less than 0.001

Variations occur in ocean salinity due to several factors. The most common factor is the relative amount of evaporation or precipitation in an area. If there is more evaporation than precipitation then the salinity increases (since salt is not evaporated into the atmosphere). If there is more precipitation (rain) than evaporation then the salinity decreases. Another factor that can change the salinity in the ocean is due to a very large river emptying into the ocean. The runoff from most small streams and rivers is quickly mixed with ocean water by the currents and has little effect on salinity. But large rivers (like the Amazon River in South America) may make the ocean have little or no salt content for over a mile or more out to sea. The freezing and thawing of ice also affects salinity. The thawing of large icebergs (made of frozen fresh water and lacking any salt) will decrease the salinity while the actual freezing of seawater will increase the salinity temporarily. This temporary increase happens in the first stages of the freezing of seawater when small ice crystals form at about minus 2 degrees Centigrade. These tiny, needle-like ice crystals are frozen freshwater and the salts are not part of them so the liquid between these crystals becomes increasingly salty to the point of it being a brine. Eventually though, as seawater freezes, the ice crystals trap areas with brine and the entire large piece of frozen seawater (ice floe) is salty.

Temperature, salinity and pressure affect the density of seawater. Large water masses of different densities are important in the layering of the ocean water (more dense water sinks). As temperature increases water becomes less dense. As salinity increases water becomes more dense. As pressure increases water becomes more dense. A cold, highly saline, deep mass of water is very dense whereas a warm, less saline, surface water mass is less dense. When large water masses with different densities meet the denser water mass slips under the less dense mass. These responses to density are the reason for some of the deep ocean circulation models The concentration of dissolved oxygen and carbon dioxide are very important for marine life forms. Although both oxygen and carbon dioxide are a gas when outside the water, they dissolve to a certain extent in liquid seawater. Dissolved oxygen is what animals with gills use for respiration (their gills extract the dissolved oxygen from the water flowing over the gill filaments). Dissolved carbon dioxide is what marine plants use for photosynthesis.

The amount of dissolved gases varies according to the types of life forms in the water. Most living species need oxygen to keep their cells alive (both plants and animals) and are constantly using it up. Replenishment of dissolved oxygen comes from the photosynthetic activity of plants (during daylight hours only) and from surface diffusion (to a lesser extent). If there are a large number of plants in a marine water mass then the oxygen levels can be quite high during the day. If there are few plants but a large number of animals in a marine water mass then the oxygen levels can be quite low. Oxygen is measured in parts per million (also called ppm) and levels can range from zero to over 20 ppm in temperate waters. It only reaches 20 when there are a lot of plants in the water, it is very sunny with lots of nutrients, and the wind is whipping up the surface into a froth. In any water mass there is a maximum amount of dissolved gas that can be found (after which the gas no longer dissolves but bubbles to the surface). This maximum amount increases with a decrease in temperature (thus cold water masses can hold more dissolved gases . . . but they can also have none if it has been used up). So, just because a water mass is cold it does not mean it has a lot of dissolved gases. This concept is a little tricky but just remember that the amount of dissolved gases in seawater depends more on the types of life forms (plants and animals) that are present and their relative proportions.

Fertilizers, like nitrogen (N), phosphorous (P), and potassium (K), are important for plant growth and are called "nutrients." The level of dissolved nutrients increases from animal feces and decomposition (bacteria, fungi). Surface water often may be lacking in nutrients because feces and dead matter tend to settle to the bottom of the ocean. Most decomposition is thus at the bottom of the ocean. In the oceans most surface water is separated from bottom water by a thermocline (seasonal in temperature and marginal polar regions, constant in tropics) which means that once surface nutrients get used up (by the plants there) they become a limiting factor for the growth of new plants. Plants must be at the surface for the light. Nutrients are returned to surface waters by a special type of current called 'upwelling' and it is in these areas of upwelling that we find the highest productivity of marine life.

Silica and iron may also be considered important marine nutrients as their lack can limit the amount of productivity in an area. Silica is needed by diatoms (one of the main phytoplanktonic organisms that forms the base of many marine food chains. Iron is just recently being discovered to be a limiting factor for phytoplankton.

pH is a measure of the acidity or alkalinity of a substance and is one of the stable measurements in seawater. Ocean water has an excellent buffering system with the interaction of carbon dioxide and water so that it is generally always at a pH of 7.5 to 8.5. Neutral water is a pH of 7 while highly acid substances are less than 7 (down to 1) and highly alkaline substances are more than 7 (up to 14). Anything either highly acid or alkaline would kill marine life but the oceans are very stable with regard to pH. If seawater was out of normal range (7.5-8.5) then something would be wrong.

Attached hereto as Appendix C is a chart listing the composition of sea water, and attached hereto as Appendix D is a chart providing the detailed composition of sea water at 3.5% salinity.

Water activity is a critical factor that determines the capability for microbial growth. While temperature, pH and several other factors can influence if and how fast organisms will grow, water activity may be the most important factor in controlling growth. Most bacteria, for example, do not grow at water activities below 0.91 $A_w$, and most molds cease to grow at water activities below 0.80 $A_w$. By measuring water activity, it is possible to predict which microorganisms will and will not grow. Water activity—not water content—determines the lower limit of available water for microbial growth.

Water activity describes the continuum of energy states of the water in a system. The water in a sample appears to be "bound" by forces to varying degrees. This is a continuum of energy states, rather than a static "boundness." Water activity is sometimes defined as "free", "bound", or "available water" in a system. These terms are easier to conceptualize, although they fail to adequately define all aspects of the concept of water activity. Water activity instruments measure the amount of free (sometimes referred to as unbound or active) water present in the sample. A portion of the total water content present in a product is strongly bound to specific sites on the chemicals that comprise the product. These sites may include the hydroxyl groups of polysaccharides, the carbonyl and amino groups of proteins, and other polar sites. Water is held by hydrogen bonds, ion-dipole bonds, and other strong chemical bonds. Some water is bound less tightly, but is still not available (as a solvent for water-soluble food components). Many preservation processes attempt to eliminate spoilage by lowering the availability of water to microorganisms. Reducing the amount of free- or unbound-water also minimizes other undesirable chemical changes that occur during storage. The processes used to reduce the amount of free water in consumer products include techniques like concentration, dehydration and freeze drying. Freezing is another common approach to controlling spoilage. Water in frozen foods is in the form of ice crystals and therefore unavailable to microorganisms for reactions with food components. Because water is present in varying degrees of free and bound states, analytical methods that attempt to measure total moisture in a sample don't always agree. Therefore, water activity tells the real story.

Enzyme and protein stability is influenced significantly by water activity due to their relatively fragile nature. Most enzymes and proteins must maintain conformation to remain active. Maintaining critical water activity levels to prevent or entice conformational changes is important to food quality. Most enzymatic reactions are slowed down at water activities below 0.8. But some of these reactions occur even at very low water activity values. This type of spoilage can result in formation of highly objectionable flavors and odors. Of course, for products that are thermally treated during processing, enzymatic spoilage is usually not a primary concern.

The moisture content of a product can be defined as the percentage weight of water in relation to the dry weight of the product. Products in which moisture can be present can be classified in two categories: hygroscopic and non hygroscopic. Examples of hygroscopic materials are salts, vegetal fibers, most metal oxides, many polymers, etc. Examples of non-hygroscopic products are metal powders, glass granules, etc. Regarding the moisture content of a product, we define static equilibrium as a set of conditions under which the product does not exchange any moisture with its environment. Under conditions of static equilibrium, the moisture content of a hygroscopic product depends on the nature of the product and also on the two following factors: (a) the partial pressure of water vapor in the immediate environment of the product; and (b) the temperature of the product. If the moisture content of a product is not dependent on both these factors, then the product is not hygroscopic.

Hygroscopic products may absorb water in different ways: sorption with formation of a hydrate, binding by surface energy, diffusion of water molecules in the material structure, capillary condensation, formation of a solution, etc. Depending on the absorption process, water is bound to the product with more or less strength. Moisture content can include both an immobilized part (e.g. water of hydration) and an active part. Water activity $A_w$ (or equilibrium relative humidity % ERH) measures the vapor pressure generated by the moisture present in a hygroscopic product.

$$Aw=p/ps \text{ and } \% ERH=100 \times Aw, \text{ where:}$$

p: partial pressure of water vapor at the surface of the product; and
ps: saturation pressure, or the partial pressure of water vapor above pure water at the product temperature.

Water activity reflects the active part of moisture content or the part which, under normal circumstances, can be exchanged between the product and its environment. Water activity is usually defined under static conditions of equilibrium. Under such conditions, the partial pressure of water vapor (p) at the surface of the product is equal to the partial pressure of water vapor in the immediate environment of the product. Any exchange of moisture between the product and its environment is driven by a difference between these two partial pressures. Finally, water vapor can also be present in a gas or gas mixture. The relative humidity of a gas is defined as % RH=100×p/ps, where (p) is the partial pressure of the water vapor present in the gas mixture and (ps) is the saturation pressure, or the partial pressure of water vapor above pure water at the temperature of the gas.

A first aspect of the present invention includes packaging live ocean water (or alternatively live fresh water) according to the following steps:

1. Obtaining live water from a natural aquatic environment;
2. Adding a nutrient enrichment solution (optional);
3. Filtering the live water to remove contaminants, particulate matter, plankton and algae; and
4. Concentrating the live water (optional);
3. Packaging the Live Water in Sealed Containers.

It has been found that bacteria, found in water obtained from a natural aquatic environment, is metabolically and physiologically active upon introduction into an aquarium environment. The present invention thus provides an optimal saltwater (or fresh water) solution and packaging method that results in the preservation of autotrophic marine bacteria in their natural habitat, i.e. in solution. It is significant to the rapid cycling of aquarium tanks that the bacteria exist in their natural state so as to be instantly capable of cycling harmful metabolic endproducts upon introduction into the aquarium environment. As used herein, the terms seawater, saltwater, and ocean water are considered synonyms.

Figure 6:
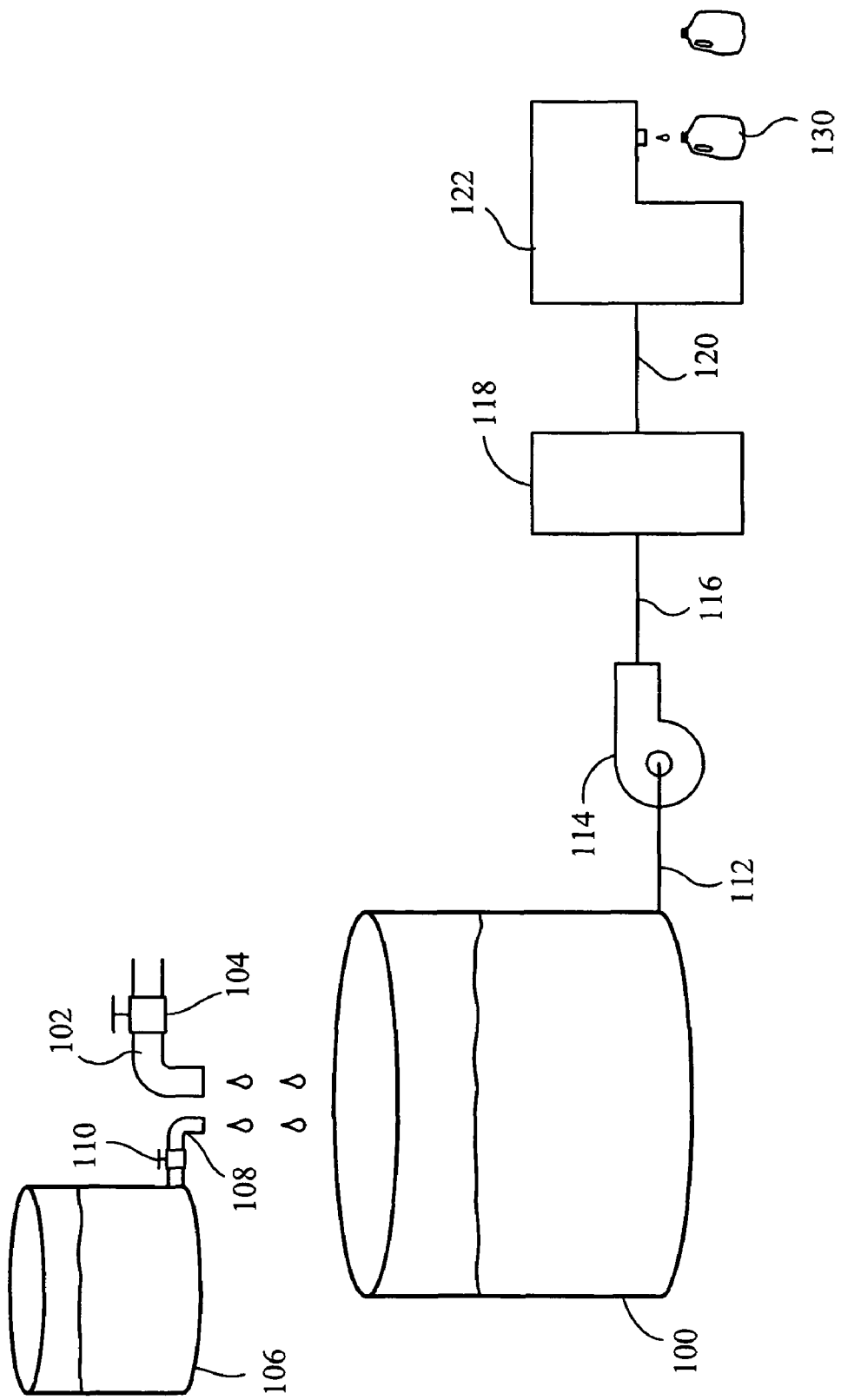
FIG. 6 illustrates processing of seawater to produce a live water product.
Figure 7:
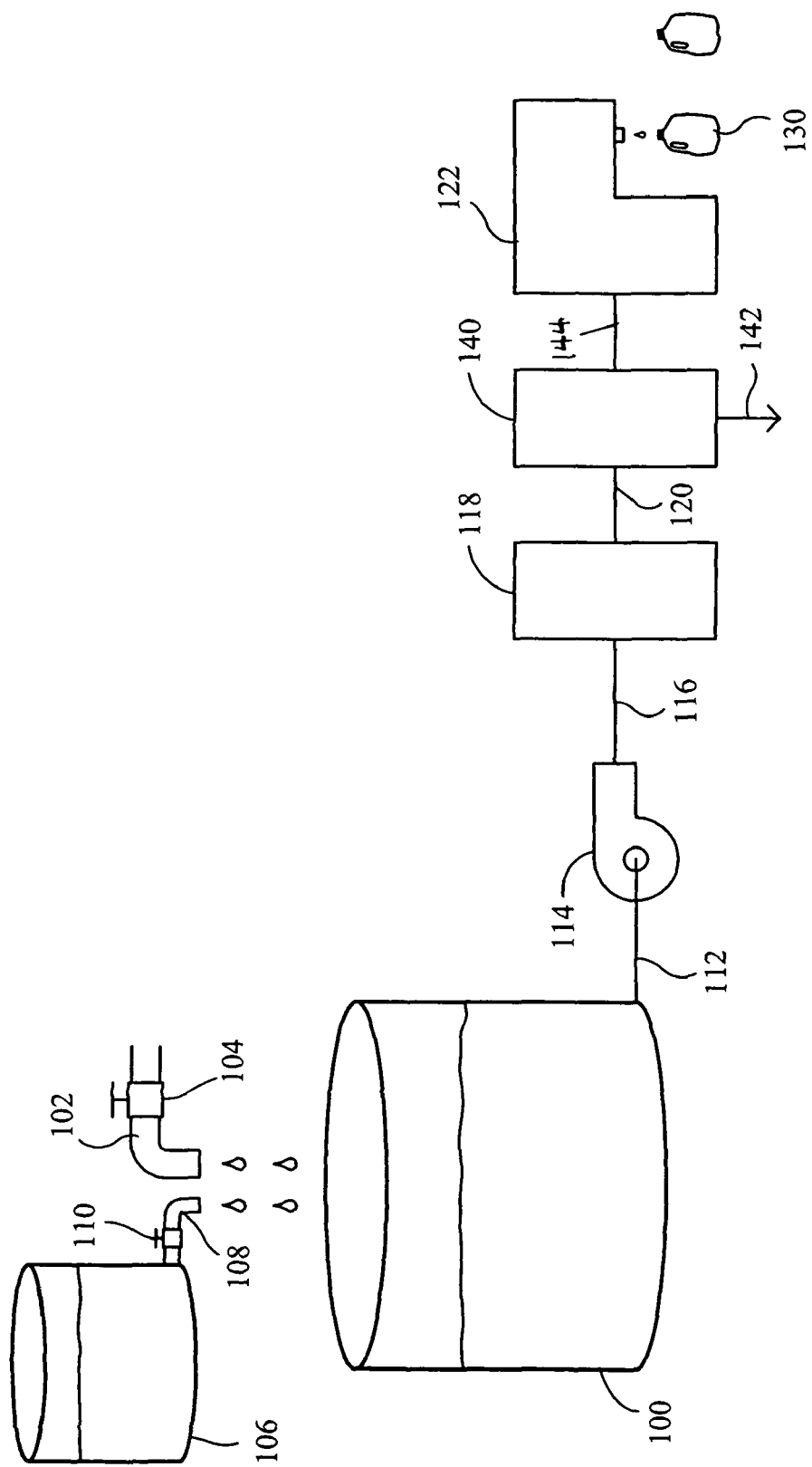
FIG. 7 illustrates processing of seawater to produce a concentrated live water product.

FIGS. 6 and 7 depict a process for producing live water, either fresh or salt, in accordance with the present invention. The process will be described in detail in connection with seawater, but the present invention is equally suitable for use with fresh water. Initially, seawater is obtained from a natural source, such as the ocean, wherein marine bacteria are present in suspension. In addition, seawater may contain a variety of other things such as contaminants, debris, oil, plankton and other aquatic life forms. As best depicted in FIG. 6, the seawater is temporarily stored in a large tank, such as a 500 gallon tank referenced 100. Tank 100 may be filled from a larger holding tank or tanker truck by a fill pipe 102 having a valve 104 for selectively allowing flow into tank 100. In one embodiment, the water stored in tank 100 may supplemented with an enrichment solution from an enrichment solution tank 106 having an outlet pipe 108 configured to discharge a selected amount of enrichment solution into tank 100 from tank 106 via a control valve 110. In a preferred embodiment the volume of enrichment solution ranges from a minimum of approximately 0.1-fluid ounce to a maximum of approximately 2-fluid ounces per gallon of seawater. In an embodiment wherein the seawater is enriched, the enrichment solution may include some or all of the elements and substances disclosed herein, either alone or in combination. While use of an enrichment solution is preferred to maximize shelf live of the finished product, the present invention is equally adapted to produce a live water product without an enrichment solution.

A significant aspect of the present invention involves filtering the seawater to remove contaminants and especially algae and plankton. More particularly, a pump 114 draws seawater from tank 100 via pipe 112 and pumps water through pipe 116 to a filter 118. Filter 118 is preferably a particulate filter having a media pore size of 5 to 20 microns. Such a pore size has been found to remove undesirable elements such as algae and plankton. Filter 118 functions to remove particulate matter, such as contaminants and plankton. Removing larger life forms such as plankton is important in providing a product that will not turn foul over time. More particularly, it has been found that unfiltered live water containing plankton spoils thereby producing a foul odor and color over time when packaged in a sealed container. The present inventors have found that the spoiling is largely the result of plankton decay. Another significant advantage realized by removing plankton and algae is to prevent those organisms from blooming once packaged thereby spoiling the water. Significantly, the bacteria that are necessary for rapid cycling of an aquarium pass through the filter and remain in the water.

The filtered water is then passed via pipe 120 to a filling machine 122. Filling machine 122 functions to fill individual containers 130 with the filtered live water. While the containers may be of any suitable size, in the preferred embodiment 1-Gallon containers having removable caps are used. The containers are preferably opaque or otherwise structured so as to protect the live water contained therein from harmful ultraviolet rays.

FIG. 7 depicts an alternate embodiment process for producing a concentrated live water product. As best depicted in FIG. 7, the seawater is temporarily stored in a large tank, such as a 500 gallon tank referenced 100. Tank 100 may be filled from a larger holding tank or tanker truck by a fill pipe 102 having a valve 104 for selectively allowing flow into tank 100. In one embodiment, the water stored in tank 100 may supplemented with an enrichment solution from an enrichment solution tank 106 having an outlet pipe 108 configured to discharge a selected amount of enrichment solution into tank 100 from tank 106 via a control valve 110. In a preferred embodiment the volume of enrichment solution ranges from a minimum of approximately 0.1-fluid ounce to a maximum of approximately 2-fluid ounces per gallon of seawater. In an embodiment wherein the seawater is enriched, the enrichment solution may include some or all of the elements and substances disclosed hereinabove, either alone or in combination. While use of an enrichment solution is preferred to maximize shelf life of the finished product, the present invention is equally adapted to produce a live water product without an enrichment solution.

A pump 114 draws seawater from tank 100 via pipe 112 and pumps water through pipe 116 to a filter 118. Filter 118 is preferably a particulate filter having a media pore size of 5 to 20 microns. Filter 118 functions to remove particulate matter, such as contaminants, plankton and algae for the reasons discussed herein. The filtered water is then passed via pipe 120 to a desalinization apparatus 140. Desalinization apparatus 140 may comprise a reverse osmosis device that converts salt water to fresh water by forcing salt water through a membrane. Desalinization apparatus 140 thus includes an output 142 for desalinated fresh water, while producing concentrated salt water as a byproduct. In a preferred embodiment, the concentration level is 0.8 $a_w$ (water activity) or above, as we have found that, at 0.8 $a_w$ and above, bacteria are capable of maintaining of metabolic and physiologic activity after prolonged periods at room temperature. However, at levels below 0.8 $a_w$ the salinity levels are such that the bacteria does not survive for extended periods of time.

The concentrated salt water is discharged from an outlet 144 and routed to a filling machine 122. Filling machine 122 functions to fill individual containers 130 with the filtered live water. While the containers may be of any suitable size, in the preferred embodiment 1-Gallon containers having removable caps are used. The containers are preferably opaque or otherwise structured so as to protect the live water contained therein from harmful ultraviolet rays. In contemplated alternate embodiments seawater may be concentrated by other suitable methods, such as flash evaporation and rotary evaporation.

The above-referenced methods each are capable of producing a live water product wherein microorganisms existing in the water are capable, upon introduction into an aquarium, to enhancing water quality by reducing harmful levels of ammonia by contributing to the nitrogen cycle.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A live saltwater composition for use in aquariums to establish a chemically balanced aquatic environment capable of supporting marine life, said composition including:
    water obtained from a natural saltwater aquatic environment, said water containing microorganisms in suspension therein;
    approximately 0.1-2.0 fluid ounces of enrichment solution per gallon of saltwater, said enrichment solution including $NaNO_3$, $NaH_2PO_4H_2O$, trace metals, vitamins, and organic stock compounds;
    said water having been filtered through a filter media having a pore size between 5 and 20 microns so as to remove certain organisms and contaminants;
    said water packaged in a sealed container for retail sale, said sealed container being opaque to ultraviolet radiation wherein the microorganisms in said water remain metabolically and physiologically active for extended periods of time in excess of twelve months in the sealed container at room temperature;
    said container including indica indicating that said water contained therein is effective in bio-cycling of the aquarium environment by stabilizing ammonia levels thereby resulting in an aquarium environment which is suitable for supporting aquatic life.

2. A live water composition according to claim 1, wherein said saltwater is concentrated by desalinization.

3. A live water composition according to claim 2, wherein said water is concentrated to a level of not less than 0.8 $a_w$.

4. A live water composition according to claim 3, wherein said saltwater is concentrated to a level between 4.0% and 8.0% total dissolved solids.

* * * * *